United States Patent [19]
Lee

[11] Patent Number: 5,108,406
[45] Date of Patent: Apr. 28, 1992

[54] INSTRUMENT TO RETRIEVE INTRALUMINAL OBJECTS

[75] Inventor: Ling H. Lee, Memphis, Tenn.
[73] Assignee: L.P. Wagi, Memphis, Tenn.
[21] Appl. No.: 627,410
[22] Filed: Dec. 14, 1990
[51] Int. Cl.⁵ .................... A61B 17/22; A61B 17/28; A61B 17/50
[52] U.S. Cl. .................... 606/106; 606/113; 606/127; 606/206
[58] Field of Search .................... 606/205–208, 606/113, 170, 106, 144, 148, 127

[56] References Cited
U.S. PATENT DOCUMENTS 1,606,497  11/1926  Berger .................... 606/113
4,923,461  5/1990  Caspari et al. .................... 606/148 X
4,935,027  6/1990  Yoon .................... 606/148 X Primary Examiner—Michael H. Thaler

[57] ABSTRACT

For the purpose of retrieving intraluminal and intracavitary objects under fluoroscopic or endoscopic guidance, a catheter assembly comprising a catheter and a transcatheter mandrel-wire combination of first grasping and then tightly snaring the object.

2 Claims, 1 Drawing Sheet

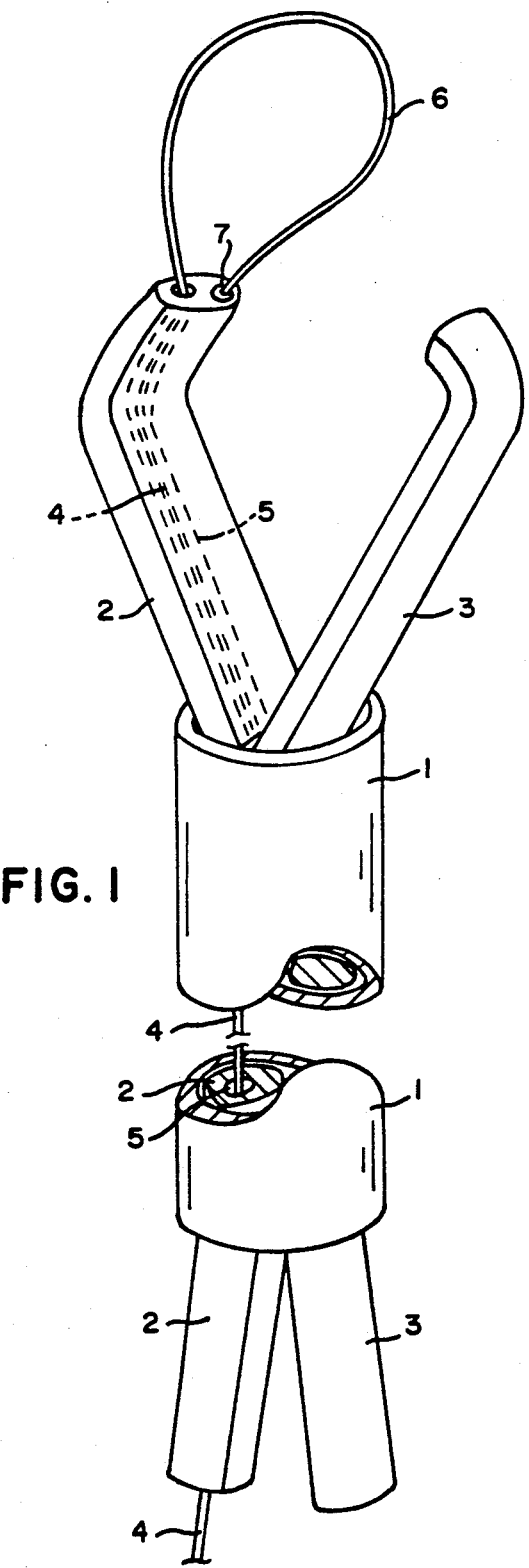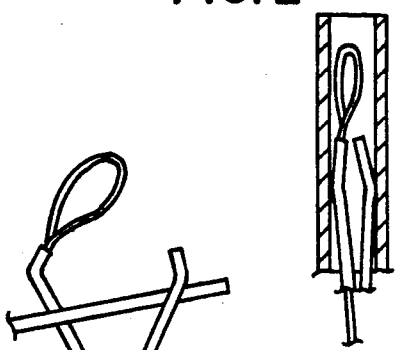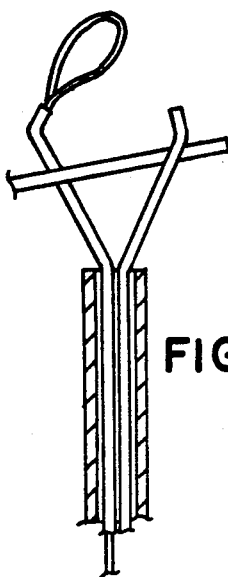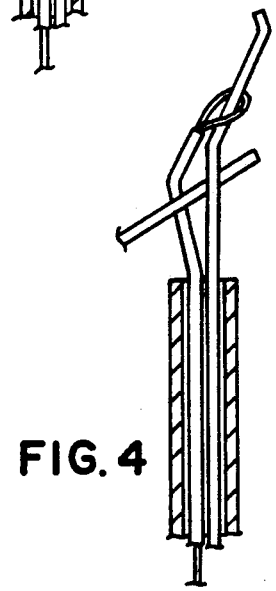

INSTRUMENT TO RETRIEVE INTRALUMINAL OBJECTS

BACKGROUND OF THE INVENTION

1. Field of the Invention

The field of this invention relates to an instrument to retrieve intraluminal objects, more particularly concerns a transcatheter instrument assembly to retrieve intraluminal foreign objects under fluoroscopic or endoscopic guidance by a grabber-converting-to-snare action.

2. Background of the Invention

There are only three types of instruments to retrieve intraluminal objects under fluoroscopic or endoscopic guidance: (a) a loop snare that is threaded into and through a catheter, (b) a modified mechanic's grabber that is threaded into and through a catheter, and (c) a wire basket that is threaded into and through a catheter. The present invention essentially incorporates all the features of the existing instruments and introduces additional advantageous features as will be apparent in the following description. A search in the patent classes/subclasses 604/52 and 604/53 did not reveal any relevant disclosures.

SUMMARY OF THE INVENTION

The present invention discloses an improved catheter assembly for the purposes of retrieving intraluminal or intracavitary foreign objects under fluoroscopic or endoscopic guidance comprising (a) a flexible radioopaque catheter, (b) to be threaded into and through the catheter a longer flexible mandrel which is split into two halves along its longitudinal axis, said mandrel at the distal end being preformed to flare to a jaw-like configuration when the distal end is exposed beyond the tip of the catheter, and (c) one end of a fine wire is anchored at the distal tip of one of the two half mandrels, while the remaining fine wire is prethreaded through the central channel within the said half mandrel. After the object is engaged within the open distal jaw, the tip of the second half mandrel is manuevered distalward into the adjustable wire loop which is then can be tightened by gradually extracting the proximally exposed fine wire. A closed snare is thus accomplished around the object.

DESCRIPTION OF THE DRAWINGS

FIG. 1 is a perspective view of the deployed assembly.

FIG. 2 is a diagram of the collapsed mandrel/wire being threaded distalward inside the catheter.

FIG. 3 is a diagram of the mandrel jaw having engaged the object.

FIG. 4 is a diagram of right half mandrel having been manipulated through the adjustable wire loop at the distal end of the left half mandrel and the partially closed wire loop.

DESCRIPTION OF THE EMBODIMENT AND FUNCTION OF THE COMPONENTS

To accomplish the aforementioned objective, the catheter assembly comprises, as depicted in FIG. 1, (1) a flexible and radioopaque catheter 1 having a proximal (exterior) end and a distal end which is introduced in the lumen or body cavity as knowledgeable to those skilled in the art. (2) to be introduced into the catheter, a longer flexible mandrel which is split into two halves, the right half 3 and the left half 2 along the longitudinal axis. The distal segments of both half mandrels are preformed to flare out to a jaw when they are exposed beyond the distal tip of the catheter 1. A channel 5 is provided through the entire length of the left half mandrel, and (3) a long small spring wire 4 one end of which is anchored at 7 at the distal end of the left half mandrel 2; while the remaining segment of the wire 4 is positioned within the channel 5. An adjustable closed wire loop 6 is thus formed at the distal end of the left half mandrel 2.

FIG. 2 depicts the collapsed jaw and the collapsed wire loop being threaded through the lumen of the catheter. FIG. 3 depicts the deployed jaw having engaged the object. The jaw is then closed gradually by gradual withdrawal of the entire mandrel. The size of the wire loop can be adjusted by pulling or pushing the wire at its proximal exposed end, if necessary. FIG. 4 depicts the distal tip of the right half mandrel having been manipulated distalward through the adjustable wire loop forming a closed snare around the object. The wire loop then can be tightened against the right half mandrel. The object is then tightly grasped by gradually extracting the entire mandrel against the distal tip of the catheter.

Manipulating the loop of existing simple loop snare device over the object (particularly an linear object) is often very difficult and sometimes impossible. It is a matter of chance that the object fits into or be manipulated into the wire basket device. As the mandrel of the ordinary modified machanic's grabber has to be threaded through the catheter, its grabbing action is weak. This presently proposed embodiment has some obvious and advantageous features.

My invention resides not in any one of these features per se, but rather in the particular combination of all of them herein disclosed and claimed and it is distinguished from prior art in this particular combination of all its structures for the functions specified. Those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent construction and obvious derivatives insofar as they do not depart from the scope and the spirit of the present invention.

Having described my invention, I claim:

1. For the purpose of retrieving intraluminal objects an assembly of cooperatively functioning components comprising:
   (a) an elongated, flexible and radioopaque catheter having a proximal (exterior) end and a distal end and having a round lumen,
   (b) a somewhat longer and round mandrel made of spring steel slideably fitting the said catheter, said mandrel being split along its longitudinal axis into a right half and a left half, the distal segments of the said two half mandrels being preformed to flare out to a V-shaped jaw when the said distal segments are exposed beyond the distal tip of the said catheter, a small channel being provided through the entire length of the said left half mandrel, and
   (c) a fine spring wire longer than the said mandrel, slideably fitting inside the said channel, the distal tip of the said spring wire being anchored permanently at the distal tip of the said left half mandrel thus forming an adjustable loop at the distal tip of the said left mandrel.

2. A method of retrieving intraluminal or intracavitory objects under fluouroscopic or endoscopic guidance utilizing said assembly as set forth in claim 1 by the following substantially sequential steps: (a) introducing said catheter into the lumen or cavity as knowledgeable to those skilled in the art, (b) introducing the collapsed tip of said mandrel and said wire loop into and through said catheter, (c) exposing the distal segment of said mandrel beyond the distal tip of said catheter, (d) engaging the object inside said V-shaped jaw, (e) gradually closing said jaw by gradually extracting said mandrel, (f) if necessary, adjusting the size of said wire loop by pushing or pulling said spring wire at its proximal end, (g) threading the distal tip of the said right half mandrel through said wire loop, (h) tightening said wire loop by pulling the proximal and exposed end of the said spring wire, and (i) snaring tightly the object against the tip of said catheter by pulling the exposed proximal end of the said mandrel.

* * * * *